US008962509B2

(12) United States Patent
Kallio et al.

(10) Patent No.: US 8,962,509 B2
(45) Date of Patent: Feb. 24, 2015

(54) PREPARATION OF A SOLID CATALYST SYSTEM

(75) Inventors: Kalle Kallio, Porvoo (FI); Marja Mustonen, Koskenkylän saha (FI); Pertti Elo, Helsinki (FI); Peter Denifl, Helsinki (FI); John Severn, Helsinki (FI)

(73) Assignee: Borealis AG, Vienna (AT)

( * ) Notice: Subject to any disclaimer, the term of this patent is extended or adjusted under 35 U.S.C. 154(b) by 50 days.

(21) Appl. No.: 13/695,884

(22) PCT Filed: Apr. 28, 2011

(86) PCT No.: PCT/EP2011/056705
§ 371 (c)(1),
(2), (4) Date: Dec. 4, 2012

(87) PCT Pub. No.: WO2011/138214
PCT Pub. Date: Nov. 10, 2011

(65) Prior Publication Data
US 2013/0253152 A1 Sep. 26, 2013

(30) Foreign Application Priority Data
May 7, 2010 (EP) .................................... 10162241

(51) Int. Cl.
| | | |
|---|---|---|
| *C08F 4/602* | (2006.01) | |
| *C08F 4/642* | (2006.01) | |
| *C08F 4/6592* | (2006.01) | |
| *C08F 10/00* | (2006.01) | |
| *C08F 4/76* | (2006.01) | |
| *C07F 5/06* | (2006.01) | |
| *C08F 4/52* | (2006.01) | |
| *B01J 31/12* | (2006.01) | |
| *B01J 31/14* | (2006.01) | |
| *B01J 31/22* | (2006.01) | |
| *B01J 31/26* | (2006.01) | |

(52) U.S. Cl.
CPC ................ *C08F 4/76* (2013.01); *C08F 4/6028* (2013.01); *B01J 31/124* (2013.01); *B01J 31/128* (2013.01); *B01J 31/143* (2013.01); *B01J 31/2295* (2013.01); *B01J 31/26* (2013.01); *B01J 2531/46* (2013.01); *B01J 2531/48* (2013.01); *B01J 2531/49* (2013.01); *B01J 2531/90* (2013.01); *B01J 2531/94* (2013.01); *C07F 5/068* (2013.01); *C08F 4/6592* (2013.01); *C08F 4/65922* (2013.01); *C08F 10/00* (2013.01); *C08F 2410/01* (2013.01); *C08F 4/52* (2013.01); *Y10S 526/943* (2013.01)
USPC ........... 502/104; 502/103; 502/152; 526/160; 526/165; 526/348; 526/943

(58) Field of Classification Search
CPC .... C08F 4/6592; C08F 4/65912; C08F 4/602; C08F 4/642; C08F 10/00
USPC .......... 502/103, 104, 152; 526/160, 165, 348, 526/943
See application file for complete search history.

(56) References Cited

U.S. PATENT DOCUMENTS

| | | | |
|---|---|---|---|
| 4,665,208 A | 5/1987 | Welborn, Jr. et al. | |
| 4,874,734 A | 10/1989 | Kioka et al. | |
| 4,908,463 A | 3/1990 | Bottelberghe | |
| 4,924,018 A | 5/1990 | Bottelberghe | |
| 4,952,540 A | 8/1990 | Kioka et al. | |
| 4,968,827 A | 11/1990 | Davis | |
| 5,091,352 A | 2/1992 | Kioka et al. | |
| 5,103,031 A | 4/1992 | Smith, Jr. | |
| 5,157,137 A | 10/1992 | Sangokoya | |
| 5,204,419 A | 4/1993 | Tsutsui et al. | |
| 5,206,199 A | 4/1993 | Kioka et al. | |
| 5,235,081 A | 8/1993 | Sangokoya | |
| 5,248,801 A | 9/1993 | Sangokoya | |
| 5,308,815 A | 5/1994 | Sangokoya | |
| 5,329,032 A | 7/1994 | Tran et al. | |
| 5,391,793 A | 2/1995 | Marks et al. | |
| 5,693,838 A | 12/1997 | Sangokoya et al. | |
| 5,731,253 A | 3/1998 | Sangokoya | |
| 5,731,451 A | 3/1998 | Smith et al. | |
| 5,744,656 A | 4/1998 | Askham | |

(Continued)

FOREIGN PATENT DOCUMENTS

| | | |
|---|---|---|
| EP | 0260130 A1 | 3/1988 |
| EP | 0279586 A2 | 8/1988 |
| EP | 0423101 A2 | 4/1991 |

(Continued)

OTHER PUBLICATIONS

International Search Report and Written Opinion for International Application No. PCT/EP2011/056705 Filed on Apr. 28, 2011.
John D. Holbrey, W. Matthew Reichert, Mark Nieuwenhuyzen, Oonagh Sheppard, Christopher Hardacre & Robin D. Rogers, Liquid clathrate formation in ionic liquid-aromatic mixitures, 2003, pp. 476-477, The Royal Society of Chemistry.
Scott K. Spear, John D. Holbrey & Robin D. Rogers, Liquid Clathrates, 2001, pp. 804-808, Encyclopedia of Supramolecular Chemistry, The University of Alabama, Tuscaloosa, Alabama.

Primary Examiner — Caixia Lu
(74) Attorney, Agent, or Firm — Warn Partners, P.C.

(57) ABSTRACT

Process for the preparation of a solid catalyst system (CS) comprising the steps of preparing a liquid clathrate (LC) comprising (a) a lattice (L) being the reaction product of (i) aluminoxane (A), (ii) an organometallic compound (O) of a transition metal (M) of Group 3 to 10 of the Periodic Table (IUPAC 2007) or of an actinide or lanthanide, and (i) a compound (B) being effective to form with the aluminoxane (A) and the organometallic compound (O) the lattice (L), and (b) a guest (G) being an hydrocarbon compound (HC), and subsequently precipitating said liquid clathrate (LC) obtaining said solid catalyst system (SC).

16 Claims, 2 Drawing Sheets

(56) References Cited

U.S. PATENT DOCUMENTS

| | | |
|---|---|---|
| 5,922,631 A | 7/1999 | Sangokoya |
| 6,277,778 B1 | 8/2001 | Leino et al. |

FOREIGN PATENT DOCUMENTS

| | | | |
|---|---|---|---|
| EP | 0537130 | A1 | 4/1993 |
| EP | 0561476 | A1 | 9/1993 |
| EP | 0594218 | A1 | 4/1994 |
| EP | 2186832 | A1 | 5/2010 |
| WO | 9410180 | A1 | 5/1994 |
| WO | 9613529 | A1 | 5/1996 |
| WO | 9710248 | A1 | 3/1997 |
| WO | 9846616 | A1 | 10/1998 |
| WO | 9849208 | A1 | 11/1998 |
| WO | 9856831 | A1 | 12/1998 |
| WO | 9910353 | A1 | 3/1999 |
| WO | 9912981 | A1 | 3/1999 |
| WO | 9919335 | A1 | 4/1999 |
| WO | 9941290 | A1 | 8/1999 |
| WO | 0034341 | A2 | 6/2000 |
| WO | 0170395 | A2 | 9/2001 |
| WO | 02060963 | A1 | 8/2002 |
| WO | 9728170 | A1 | 3/2003 |
| WO | 03051934 | A2 | 6/2003 |
| WO | 03082879 | A1 | 10/2003 |

Figure 1: Particles directly from silicon fluid slurry after spraying (example 1).

Figure 2: Light microscope picture from glass bottle where catalyst has settled onto bottles internal surface (catalyst of example 1)

Figure 3:    Catalyst particles (example 2)

Figure 4:    polymer particles (example 3)

PREPARATION OF A SOLID CATALYST SYSTEM

CROSS REFERENCE TO RELATED APPLICATIONS

This application is a National Stage of International Application No. PCT/EP2011/056705, filed Apr. 28, 2011. This application claims priority to European Patent Application No. 10162241.3 filed on May 7, 2010. The disclosures of the above applications are incorporated herein by reference.

The present invention is directed to a new method for preparing a solid catalyst system enabling the preparation of polymers with high bulk density and catalysts prepared thereof.

In the field of catalysts since many years great efforts are undertaken to further improve the catalyst types tailored for specific purposes. For instance in polymerization processes metallocene catalyst systems are widely used having many advantages.

At the beginning of the development of new metallocene catalyst systems only homogeneous catalyst systems were available. Such homogeneous catalyst systems are solutions of one or more catalyst components, e.g. a transition metal compound and optionally a cocatalyst. Homogeneous systems are used as liquids in the polymerization process. Such systems have in general a satisfactory catalytic activity, but their problem has been that the polymer thus produced has a poor morphology (e.g. the end polymer is in a form of a fluff having a low bulk density). As a consequence, operation of slurry and gas phase reactors using a homogeneous catalyst system causes problems in practice for instance in terms of reactor fouling.

To overcome the problems of the homogeneous catalyst systems supported systems have been developed. These supported systems, known as heterogeneous catalyst systems, comprise carrier materials, such as porous organic and inorganic support materials, like silica, $MgCl_2$ or porous polymeric materials onto which the catalyst is loaded or supported.

However, also supported catalyst systems cause problems. For instance, to mention only one among many, it is difficult to get an even distribution of the catalyst components in the porous carrier material. Further leaching of the catalyst components from the support can occur. Such drawbacks lead to an unsatisfactory polymerization behavior of the catalyst, and as a result the morphology of the polymer product thus obtained is also poor. Further such classic heterogeneous catalyst systems show reduced catalyst activity which is of course detrimental as the catalyst amount must be increased which in turn leads to polymer products contaminated with rather high amounts of catalyst residues including silica residues, which might be very detrimental in some product applications.

For this reason a new metallocene catalyst system has been developed which significantly reduces the drawbacks of the known heterogeneous catalyst systems. Such new catalyst systems are solid catalyst systems, but are not in need of catalytically inert support material, and are further featured by spherical particles with low porosity. Such new metallocene catalyst systems enable to increase the output rate of polymers since the bulk density of the polymerized product can be increased. For the first time such new metallocene catalyst systems have been for instance described in WO 03/051934. These types of catalysts have solved many problems caused by catalysts of earlier prior art.

In addition to the catalyst types described above, there are also catalysts, where catalyst component aluminoxane, like MAO, itself forms support for the catalysts.

Many prior art catalysts have, however, a general drawback relating to their tendency to dissolve in the polymerisation medium, and thus causing undesired fouling in the reactors. Thus, there remains still some work to do to improve the properties of the catalyst especially in the morphology point of view and in a way that the desired morphology would remain and be effectively used, during the polymerization, which would also decrease fouling and sheeting problems Moreover nowadays the catalyst shall be not only suitable for specific processes for producing desired polymers but there is a general tendency to find out methods, also in catalyst preparation field, where the starting materials are safer and easier to be used both in environmental as well handling point of view. Thus there is the strong need to develop preparation methods of such catalyst systems based on materials which promote sustainable preparation method as well as are easily commercially accessible and thus well priced.

Thus the object of the present invention is to find an improved and suitable process for the manufacture of solid catalyst systems without the need of using external support materials, and which render possible to produce polymers in an efficient manner, i.e. using solid catalyst systems which are less soluble in the polymerization media and are obtained by a sustainable preparation process. A further object is that the obtained catalyst system enables to produce high bulk density polymers with narrow particle size distribution in an efficient manner.

The finding of the present invention is that the solid catalyst system must be produced by converting a liquid clathrate which contains all catalyst components into solid form by precipitation.

Thus the present invention is directed to a process for the preparation of a solid catalyst system (CS) comprising the steps of (I) preparing a liquid clathrate (LC) comprising
  (i) a lattice (L) being the reaction product of
    (α) aluminoxane (A),
    (β) an organometallic compound (O) of a transition metal (M) of Group 3 to 10 of the Periodic Table (IUPAC 2007) or of an actinide or lanthanide, and
    (γ) a compound (B) being effective to form with the aluminoxane (A) and the organometallic compound (O) the lattice (L),
  and
  (ii) a guest (G) being an hydrocarbon compound (HC), and subsequently followed by
(II) precipitating said liquid clathrate (LC) obtaining said solid catalyst system (SC).

Surprisingly it has been found out that with the above defined process in an effective manner solid catalyst systems (CS) are producible, which enables a person skilled in the art to produce polymers having good morphology. Further no reactor fouling is observed in the polymerization process in case solid catalysts are employed, which are prepared according to the instant invention. Further the inventive process is a sustainable process especially in process safety point of view.

One further remarkably aspect of the solid catalyst system (CS) obtained according to the instant process is that said solid catalyst system (CS) is solid, however, without any need of external catalytically inert support material. Inert support material according to this invention is any material which is used to decrease solubility of the catalyst systems in media which are generally used in polymerization processes. Accordingly the inert support material is a material which effectively decreases solubility in common solvents like pentane, heptane and toluene. Typical inert support materials are organic and inorganic support materials, like silica, $MgCl_2$ or porous polymeric material. These support materials are generally used in amounts of at least 50 wt.-%, more preferably of at least 70.0 wt.-%. Accordingly in the inventive process no support material is used and thus the amount of support material within the obtained solid catalyst system (CS) is below 10.0 wt.-%, yet more preferably below 5.0 wt.-%, yet more preferably not detectable.

In the following the essential features of the present invention are described in more detail.

As stated above, step (II) "subsequently follows" step (I). This expression indicates that preferably no further additional steps between step (I) and step (II) exist. In other words, in the first step (step (I)) the liquid clathrate (LC) is produced and this liquid clathrate (LC) is than in the subsequent step (step (II)) precipitated. Accordingly the requirement that step (II) must subsequently follow step (I) may allow the storage of the liquid clathrate (LC) but does not encompass embodiments in which the liquid clathrate (LC) is further treated, e.g. forming an emulsion of the liquid clathrate (LC) and an other liquid. Thus in a preferred embodiment the instant process does not comprise, preferably between step (I) and step (II), a step in which the liquid clathrate (LC) is used for the formation of an emulsion.

Therefore the present invention is in particular directed to a process for the preparation of a solid catalyst system (CS) comprising the step of precipitation, said process consisting of the steps (I) and (II) as defined in the instant invention.

The term "solution" throughout the present application indicates that two or more substances are homogenous mixed.

An "emulsion" according to this invention is a mixture of two liquid substances. One substance (the dispersed phase) is dispersed in the other (the continuous phase) as droplets.

The term "liquid" according to this invention indicates that a compound (including a liquid) is liquid by normal pressure (1 atm) at room temperature, e.g. 20 to 25° C.

A "liquid clathrate" is according to this invention a liquid which comprises, preferably consists of, a lattice (L), i.e. the reaction product of aluminoxane (A), the organometallic compound (O), and the compound (B), and a guest (G) enclosed therein. Liquid clathrates are well known and for instance described by Atwood, Jerry L. Dep. Chem., Univ. Alabama, Tuscaloosa, Ala., USA. Editor(s): Robinson, Gregory Heagward; Coord. Chem. Alum. (1993), p. 197-32. Publisher: VCH, New York, N.Y. CODEN: 59ECAI Conference; General Review written in English. CAN 119:117290; John D. Holbrey, "Liquid clathrate formation in ionic liquid-aromatic mixtures", Chem. Commun., 2003, pages 476 to 477, and Scott K. Spear, Encyclopedia of Supramolecular Chemistry, 2001, pages 804 to 807. Accordingly the "liquid clathrate (LC)" is preferably a liquid in which the lattice (L) constitutes the superstructure wherein the guest (G) is embedded. Preferably the guest (G) stabilizes said superstructure.

An additional benefit of the solid catalyst system (CS) of the present invention over the standard metallocene/MAO based catalysts is the low solubility into solvents including solvents used in polymerization, being maybe the biggest additional advantage. One finding of the present invention is that the liquid clathrate (LC) is more stable as traditional catalyst/co-catalyst structures and thus is less soluble in preferred media for precipitation.

This improved stability opens new ways for converting catalysts in liquid form into solid catalyst systems based on organometallic compounds (O).

Thus one essential aspect of the invention is that the solid catalyst is obtained by the use of a specific liquid clathrate (LC). Accordingly the liquid clathrate (LC) of the present invention comprises (a) a lattice (L) being the reaction product of
   (i) aluminoxane (A),
   (ii) an organometallic compound (O) of a transition metal (M) of Group 3 to 10 of the Periodic Table (IUPAC 2007) or of an actinide or lanthanide, and
   (iii) a compound (B) being effective to form with the aluminoxane (A) and the organometallic compound (O) the lattice (L),
and
(b) a guest (G) being an hydrocarbon compound (HC), Preferably the lattice is formed by reacting the compound (B) with the aluminoxane (A) and/or the organometallic compound (O) in the hydrocarbon compound (HC). Thus in the following the individual reactants are defined in more detail.

As stated above for the formation of the lattice (L) of the liquid clathrate (LC) a compound (B) is necessary which reacts with the aluminoxane (A) and/or the organometallic compound (O). Preferably the compound (B) is an M-X compound or an organo-silicon compound (OS) being different to the non halogenated fluid (NF), i.e. different to the silicon fluid (SF).

M-X compounds which are effecting the formation of a lattice (L) with the aluminoxane (A) and/or the organometallic compound (O) are organic, inorganic or organometallic compounds which can potentially dissociate or partially dissociate into cationic ($M^+$) and anionic components (X). Such compounds are for instance disclosed for example in WO 97/14700.

"M" can be an alkali or alkaline earth metal, like Na, K, Li, Mg or Ca, and

"X" can be a halide, like F, Cl or Br, a pseudohalide or an anionic group, like an allylic or a benzylic hydrocarbon group.

The term "pseudohalide" refers to moieties which are not halides but are generally considered to be a good leaving group in substitution reaction. Pseudohalides can include, for example, azides, cyanide, cyanate, thiocyanate, isocyanate, isothiocyanate, silicon groups, sulfur groups, nitrogen groups, oxygen groups, boron groups and phosphorous groups.

Preferred examples for M-X compounds are alkali and alkaline earth halides or pseudohalides such as KCl, KF, LiCl, $CaCl_2$, $MgCl_2$, $MgF_2$, NaF, $NaBO_4$, $KOSiR_3$, wherein R being a $C_1$ to $C_6$-alkyl residue, or KR', wherein R' is an allylic hydrocarbon group or a benzylic hydrocarbon group.

The reaction of such M-X compounds with the aluminoxane (A) and/or the organometallic compound (O), preferably in an liquid hydrocarbon compound (HC) as defined in detail below, leads to the formation of the lattice (L) of the liquid clathrate (LC).

Other examples of M-X compounds include metal hydrides such as KH, LiH and alkyl, aryl and alkyl-aryl ammonium, phosphonium, sulfonium and other organometallic salts of halides and pseudo halides such as $R_4NCl$, $MePh_3PBr$, $NaBPh_4$, $KB(C_6F_5)_4$, $LiR_4Al$, R being a $C_1$ to $C_8$-alkyl residue.

Also allylic and benzylic organolithium, organopotassium and organocesium compounds are suitable as M-X compounds. Reference is made to Organometallics in Synthesis—A Manual, $2^{nd}$ Edition, Ed. Manfred Schlosser; Wiley, (2002) p. 161 to 162, ISBM 0-471-98416-7, which is incorporated here by reference.

Preferably used M-X compounds are KCl, KF, NaF, LiCl, $CaCl_2$, $MgCl_2$, $MgF_2$, KH, LiH, $KOSiR_3$, $NaBPh_4$, $Me_4NCl$, $(Octyl)_3NClMe$, $MePh_3PBr$, $KB(C_6F_5)_4$ and $KCH_2$—$C_6H_5$ More preferably used M-X compounds are KCl, KF, NaF, $Me_4NCl$, $(Octyl)_3NClMe$, KH, $MePh_3PBr$, $NaBPh_4$, $KOSiMe_3$ and $KCH_2$—$C_6H_5$ The molar ratio of aluminum, provided by the aluminoxane (A), and M (cationic moiety), provided by the M-X compound is in the range of 1:1 to 50:1, preferably from 5:1 to 30:1 and more preferably from 8:1 to 25:1.

The organo-silicon compound (OS) which is effective to form the lattice (L) with the aluminoxane (A) and/or the organometallic compound (O) can be selected from the group of hydrocarbyloxysilanes of the formula $R_3Si$—$O[$—$SiR_2$—$O]_n$—$SiR_3$ or $Si$-$[O$—$R]_4$ wherein R is, independently, a hydrocarbyl group having up to about 18 carbon atoms (e.g. linear or branched alkyl, cycloalkyl, aryl, aralkyl) and n is 0 to 3; and hydrocarbylpolysiloxanes having from 2 to 6 silicon atoms in the molecule and which are separated from each other by an oxygen atom such that there is a linear, branched or cyclic backbone of alternating Si and oxygen atoms, with the remainder of the four valence bonds of each of the silicon atoms individually satisfied by an univalent hydrocarbyl group, R, as just defined. Preferred hydrocarbyl groups, R, are methyl, ethyl and phenyl. Examples of such organo-silicon compounds (OS) include tetra-methoxysilane, tetra-ethoxysilane, tetralphenoxysilane, methoxytrimethylsilane, ethoxytrimethylsilane, hexamethyldisiloxane, hexaethyldisiloxane, hexaphenyldisiloxane, tetramethyldiphenyldisiloxane, dimethyltetraphenyldisiloxane, hexamethylcyclotrisiloxane, octamethylcyclotetrasiloxane, octaphenylcyclotetrasiloxane, octamethyltrisiloxane, decamethyltetrasiloxane, dodecamethylpentasiloxane and tetradecamethylhexasiloxane.

Preferred organo-silicon compounds (OS) are octamethyltrisiloxane, decamethyltetrasiloxane, octamethylcyclotetrasiloxane, methoxytrimethylsilane and tetraethoxysilane.

The molar ratio of aluminum, provided by the aluminoxane (A), and the organo-silicon compound (OS) is in the range of 1:1 to 200:1, preferably from 100:1 to 5:1 and more preferably from 50:1 to 10:1.

Preferably used as compound (B) are the above described organo-silicon compounds (OS).

The aluminoxane (A) can be any conventional aluminoxane as is known in the art.

Aluminoxanes are commercially available or can be prepared according to prior art literature for example by the hydrolysis of aluminium alkyls either by direct water addition or by treatment with salt hydrates. There are a variety of methods for preparing aluminoxane and modified aluminoxanes, non-limiting examples of which are described in U.S. Pat. No. 4,665,208, U.S. Pat. No. 4,952,540, U.S. Pat. No. 5,091,352, U.S. Pat. No. 5,206,199, U.S. Pat. No. 5,204,419, U.S. Pat. No. 4,874,734, U.S. Pat. No. 4,924,018, U.S. Pat. No. 4,908,463, U.S. Pat. No. 4,968,827, U.S. Pat. No. 5,308,815, U.S. Pat. No. 5,329,032, U.S. Pat. No. 5,248,801, U.S. Pat. No. 5,235,081, U.S. Pat. No. 5,157,137, U.S. Pat. No. 5,103,031, U.S. Pat. No. 5,391,793, U.S. Pat. No. 5,391,529, U.S. Pat. No. 5,693,838, U.S. Pat. No. 5,731,253, U.S. Pat. No. 5,731,451 U.S. Pat. No. 5,744,656, EP-A-0 561 476, EP-B1-0 279 586, EP-A-0 594-218, and WO 94/10180, all of which are herein fully incorporated by reference.

Aluminoxanes are also called alumoxanes.

Preferably, $C_1$ to $C_{10}$-alkylalumoxanes, particularly methylalumoxane or modified methylalumoxane, isobutylalumoxane, e.g. TIBAO (tetraisobutylalumoxane) or HIBAO (hexaisobutylalumoxane) are used. More preferably the aluminoxane (A) is methylalumoxane (MAO).

Most preferably the aluminoxane (A) is MAO commercially available as 5 to 30 wt % solution in toluene.

The third compound used for the formation of the lattice (L) is an organometallic compound (O) of a transition metal (M) of Group 3 to 10 of the Periodic Table (IUPAC 2007) or of an actinide or lanthanide.

The term "an organometallic compound (O) of a transition metal (M)" in accordance with the present invention includes any metallocene or non-metallocene compound of a transition metal which bears at least one organic (coordination) ligand and exhibits the catalytic activity alone or together with a cocatalyst. The transition metal compounds are well known in the art and the present invention covers compounds of metals from Group 3 to 10, e.g. Group 3 to 7, or 3 to 6, such as Group 4 to 6 of the Periodic Table, (IUPAC 2007), as well as lanthanides or actinides.

Accordingly, said organometallic compound (O) of a transition metal (M) may have the following formula (I):

$$(L)_m R_n MX_q \qquad (I)$$

wherein
"M" is a transition metal as defined above, preferably Zr, Ti, or Hf,
each "X" is independently a monovalent anionic ligand, such as a σ-ligand,
each "L" is independently an organic ligand which coordinates to the transition metal "M",
"R" is a bridging group linking two ligands "L",
"m" is 1, 2 or 3,
"n" is 0, 1 or 2, preferably 0 or 1,
"q" is 1, 2 or 3, and
m+q is equal to the valency of the metal.

In a more preferred definition, each organic ligand "L" is independently
(a) a substituted or unsubstituted cyclopentadienyl or a mono-, bi- or multifused derivative of a cyclopentadienyl which optionally bear further substituents and/or one or more hetero ring atoms from a Group 13 to 16 of the Periodic Table (IUPAC); or
(b) an acyclic $\eta^1$- to $\eta^4$- or $\eta^6$-ligand composed of atoms from Groups 13 to 16 of the Periodic Table, and in which the open chain ligand may be fused with one or two, preferably two, aromatic or non-aromatic rings and/or bear further substituents; or
(c) a cyclic sigma-, $\eta^1$- to $\eta^4$- or $\eta^6$-, mono-, bi- or multidentate ligand composed of unsubstituted or substituted mono-, bi- or multicyclic ring systems selected from aromatic or non-aromatic or partially saturated ring systems, and containing carbon ring atoms and optionally one or more heteroatoms selected from Groups 15 and 16 of the Periodic Table.

More preferably at least one of the organic ligands "L", preferably both organic ligands "L", is(are) selected from the group consisting of unsubstituted cyclopentadienyl, unsubstituted indenyl, unsubstituted tetrahydroindenyl, unsubstituted fluorenyl, substituted cyclopentadienyl, substituted indenyl, substituted tetrahydroindenyl, and substituted fluorenyl.

Further in case the organic ligands "L" are substituted it is preferred that at least one organic ligand "L", preferably both organic ligands "L", comprise(s)

(a) one or more residues independently selected from the group consisting of halogen, $C_1$ to $C_{10}$ alkyl, $C_2$ to $C_{20}$ alkenyl, $C_2$ to $C_{20}$ alkinyl, $C_3$ to $C_{12}$ cycloalkyl, $C_6$ to $C_{20}$ aryl, $C_7$ to $C_{20}$-arylalkyl, $C_3$ to $C_{12}$ cycloalkyl which contains 1, 2, 3 or 4 heteroatom(s) in the ring moiety, $C_6$ to $C_{20}$ heteroaryl and $C_1$ to $C_{20}$ haloalkyl, or more preferably (b) one or more residues independently selected from the group consisting of halogen, $C_1$ to $C_{10}$ alkyl, $C_3$ to $C_{12}$ cycloalkyl, $C_6$ to $C_{20}$ aryl, $C_7$ to $C_{20}$-arylalkyl, $C_3$ to $C_{12}$ cycloalkyl which contains 1, 2, 3 or 4 heteroatom(s) in the ring moiety, $C_6$ to $C_{20}$ heteroaryl and $C_1$ to $C_{20}$ haloalkyl.

By "σ-ligand" is meant throughout the invention a group bonded to the transition metal (M) at one or more places via a sigma bond.

Further the ligands "X" are preferably independently selected from the group consisting of hydrogen, halogen, $C_1$ to $C_{20}$ alkyl, $C_1$ to $C_{20}$ alkoxy, $C_2$ to $C_{20}$ alkenyl, $C_2$ to $C_{20}$ alkynyl, $C_3$ to $C_{12}$ cycloalkyl, $C_6$ to $C_{20}$ aryl, $C_6$ to $C_{20}$ aryloxy, $C_7$ to $C_{20}$ arylalkyl, $C_7$ to $C_{20}$ arylalkenyl, —SR", —PR"$_3$, —SiR"$_3$, —OSiR"$_3$ and —NR"$_2$, wherein each R" is independently hydrogen, $C_1$ to $C_{20}$ alkyl, $C_2$ to $C_{20}$ alkenyl, $C_2$ to $C_{20}$ alkynyl, $C_3$ to $C_{12}$ cycloalkyl or $C_6$ to $C_{20}$ aryl.

Additionally the bridging group "R" may a bridge of 1 to 7 atoms length, preferably with at least one heteroatom. Accordingly the bridging group "R" is a bridge of 1 to 7 C-atoms, e.g. a bridge of 1 to 4 C-atoms and 0 to 4 heteroatoms, wherein the heteroatom(s) can be e.g. Si, Ge and/or O atom(s), whereby each of the bridge atoms may bear independently substituents, such as $C_1$ to $C_{20}$-alkyl, tri($C_1$ to $C_{20}$-alkyl)silyl, tri($C_1$ to $C_{20}$-alkyl)siloxy or $C_6$ to $C_{20}$-aryl substituents); or a bridge of 1 to 3, e.g. one or two, hetero atoms, such as Si, Ge and/or O atom(s), e.g. —SiR$^1$$_2$, wherein each R$^1$ is independently $C_1$ to $C_{20}$-alkyl, $C_6$ to $C_{20}$-aryl or tri($C_1$ to $C_{20}$-alkyl)silyl-residue, such as a trimethylsilyl-residue. It is in particular appreciated that the bridging group(s) (R) has (have) the formula (II)

—Y(R')(R")— (II)

wherein

Y is carbon (C), silicon (Si) or germanium (Ge), and R', R" are independently selected from the group consisting of is $C_1$ to $C_{20}$ alkyl, $C_4$ to $C_{10}$ cycloalkyl, $C_6$ to $C_{12}$ aryl, $C_7$ to $C_{12}$ arylalkyl, or trimethylsilyl.

According to a preferred embodiment said organometallic compound (O) of formula (I) is a group of compounds known as metallocenes. Said metallocenes bear at least one organic ligand, generally 1, 2 or 3, e.g. 1 or 2, which is η-bonded to the metal, e.g. a η$^2$- to η$^6$-ligand, such as a η$^5$-ligand.

Preferably, a metallocene according to this invention is a transition metal (M) of anyone of the groups 4 to 6 of the periodic table (IUPAC), suitably titanocene, zirconocene or hafnocene, which contains at least one η$^5$-ligand, which is an optionally substituted cyclopentadienyl, an optionally substituted indenyl, an optionally substituted tetrahydroindenyl or an optionally substituted fluorenyl. Thus the transition metal compound has preferably the formula (III)

(Cp)$_2$R$_n$MX$_2$ (III)

wherein

"M" is zirconium (Zr), hafnium (Hf), or titanium (Ti), preferably zirconium (Zr) or hafnium (Hf), each "X" is independently a monovalent anionic σ-ligand, preferably selected from the group consisting of hydrogen, halogen, $C_1$ to $C_{20}$ alkyl, $C_1$ to $C_{20}$ alkoxy, $C_2$ to $C_{20}$ alkenyl, $C_1$ to $C_{20}$ alkynyl, $C_3$ to $C_{12}$ cycloalkyl, $C_6$ to $C_{20}$ aryl, $C_6$ to $C_{20}$ aryloxy, $C_7$ to $C_{20}$ arylalkyl, $C_7$ to $C_{20}$ arylalkenyl, —SW, —PR"$_3$, —SiR"$_3$, —OSiR"$_3$ and —NR"$_2$, wherein each R" is independently hydrogen, $C_1$ to $C_{20}$ alkyl, $C_2$ to $C_{20}$ alkenyl, $C_2$ to $C_{20}$ alkynyl, $C_3$ to $C_{12}$ cycloalkyl or $C_6$ to $C_{20}$ aryl, more preferably each "X" is Cl, each "Cp" is independently an unsaturated organic cyclic ligand which coordinates to the transition metal (M), "R" is a bridging group linking two organic ligands (L), preferably the bridging group (R) has the formula (II)

"n" is 0 or 1, preferably 1, and at least one "Cp"-ligand, preferably both "Cp"-ligands, is(are) selected from the group consisting of unsubstituted cyclopentadienyl, unsubstituted indenyl, unsubstituted tetrahydroindenyl, unsubstituted fluorenyl, substituted cyclopentadienyl, substituted indenyl, substituted tetrahydroindenyl, and substituted fluorenyl, preferably substituted indenyl.

The substituted Cp-ligand(s) may have one or more substituent(s) being selected form the group consisting of halogen, hydrocarbyl (e.g. linear $C_1$ to $C_{20}$ alkyl, branched $C_3$ to $C_{20}$ alkyl, linear $C_1$ to $C_{20}$ alkenyl, branched $C_4$ to $C_{20}$ alkenyl, $C_2$ to $C_{20}$ alkinyl, $C_3$ to $C_{12}$ cycloalkyl, $C_1$ to $C_{20}$ alkyl substituted $C_5$ to $C_{20}$ cycloakyl, $C_5$ to $C_{20}$ cycloakyl substituted $C_1$ to $C_{20}$ alkyl wherein the cycloakyl residue is substituted by $C_1$ to $C_{20}$ alkyl, $C_6$ to $C_{20}$ aryl, $C_7$ to $C_{20}$ arylalkyl, $C_3$ to $C_{12}$-cycloalkyl which contains 1, 2, 3 or 4 heteroatom(s) in the ring moiety, $C_6$ to $C_{20}$-heteroaryl, $C_1$ to $C_{20}$-haloalkyl, —SiR"$_3$, —SR", —PR"$_2$ or —NR"$_2$, each R" is independently a hydrogen or hydrocarbyl (e.g. $C_1$ to $C_{20}$ alkyl, $C_1$ to $C_{20}$ alkenyl, $C_2$ to $C_{20}$ alkinyl, $C_3$ to $C_{12}$ cycloalkyl, or $C_6$ to $C_{20}$ aryl) or e.g. in case of —NR"$_3$, the two substituents R" can form a ring, e.g. five- or six-membered ring, together with the nitrogen atom wherein they are attached to.

In a suitable subgroup of the compounds of formula (III) each "Cp"-ligand independently bears one or more, like two, substituents selected from $C_1$ to $C_{20}$-alkyl, $C_5$ to $C_{20}$ cycloakyl substituted $C_1$ to $C_{20}$ alkyl wherein the cycloakyl residue is substituted by $C_1$ to $C_{20}$ alkyl, $C_6$ to $C_{20}$-aryl, $C_7$ to $C_{20}$-arylalkyl (wherein the aryl ring alone or as a part of a further moiety may further be substituted as indicated above), wherein R" is as indicated above, preferably $C_1$ to $C_{20}$-alkyl, the ligand "X" is hydrogen (H), halogen, $C_1$ to $C_{20}$-alkyl, $C_1$ to $C_{20}$-alkoxy, $C_6$ to $C_{20}$-aryl, $C_7$ to $C_{20}$-arylalkenyl or —NR"$_2$ as defined above, e.g. —N($C_1$ to $C_{20}$-alkyl)$_2$, and the bridging group "R" is a methylene, ethylene or a silyl bridge, whereby the silyl can be substituted as defined above, e.g. a dimethylsilyl=, methylphenylsilyl=, methylcylohexylsilyl=, or trimethylsilylmethylsilyl=-bridge.

Examples of compounds wherein the metal atom bears a-NR"$_2$ ligand are disclosed i.e. in WO 98/56831 and WO 00/34341. The contents of the documents are incorporated herein by reference. Further metallocenes are described e.g. in EP 260 130. As further examples of usable metallocenes may also be found e.g. from WO 97/28170, WO 98/46616, WO 98/49208, WO 99/12981, WO 99/19335, WO 98/56831, WO 00/34341, EP 423 101 and EP 537 130 as well as V. C. Gibson et al., in Angew. Chem. Int. Ed., engl., vol 38, 1999, pp 428-447, the disclosures of which are incorporated herein by reference.

In an specific embodiment the organometallic compound (O) of a transition metal (M) is a compound of formula (IV)

(Cp)$_2$RMX$_2$ (IV)

wherein

"M" is zirconium (Zr) or hafnium (Hf), each "X" is independently a σ-ligand, each "Cp" is independently an indenyl ligand which coordinates to the transition metal (M),
said indenyl ligand is substituted at least at the five membered ring (substituent (S5)) and the
six membered ring (substituent (S6)) of the indenyl ligand,
"R" is a bridging group linking said organic ligands (L).

More preferably the ligands "X" of formula (IV) can independently be selected from the group consisting of hydrogen, halogen, $C_1$ to $C_{20}$ alkyl, $C_1$ to $C_{20}$ alkoxy, $C_2$ to $C_{20}$ alkenyl, $C_2$ to $C_{20}$ alkynyl, $C_3$ to $C_{12}$ cycloalkyl, $C_6$ to $C_{20}$ aryl, $C_6$ to $C_{20}$ aryloxy, $C_7$ to $C_{20}$ arylalkyl, $C_7$ to $C_{20}$ arylalkenyl, —SW, —PR''$_3$, —SiR''$_3$, —OSiR''$_3$ and —NR''$_2$, wherein each R'' is independently hydrogen, $C_1$ to $C_{20}$ alkyl $C_2$ to $C_{20}$ alkenyl, $C_2$ to $C_{20}$ alkinyl, $C_3$ to $C_{12}$ cycloalkyl or $C_6$ to $C_{20}$ aryl. In a preferred embodiments the ligands "X" are identical and either halogen, like Cl, or benzyl.

A preferred monovalent anionic ligand of formula (IV) is halogen, in particular chlorine (Cl).

The subtituents (S6) at the six membered ring as well as the subtituents (S5) at the five membered ring are preferably on both indenyl residues the same.

Preferably the subtituents (S6) are selected from the group consisting of linear $C_1$ to $C_{20}$ alkyl, branched $C_3$ to $C_{20}$ alkyl, $C_1$ to $C_{20}$ alkyl substituted $C_5$ to $C_{20}$ cycloalkyl, $C_5$ to $C_{20}$ cycloalkyl substituted $C_1$ to $C_{20}$ alkyl wherein the cycloalkyl residue is substituted by $C_1$ to $C_{20}$ alkyl, arly, like phenyl, and substituted aryl, like substituted phenyl. More preferably the subtituents (S6) are selected from the group consisting of methyl, ethyl, n-propyl, iso-propyl, n-butyl, tert-butyl, cyclohexyl, methyl-(methyl-cyclohexyl), methylphenyl, ethylphenyl, n-propylphenyl, iso-propylphenyl, n-butylphenyl, tert-butylphenyl, cyclohexylphenyl, methyl-(methyl-cyclohexyl)-phenyl.

Preferably the subtituents (S5) are selected from the group consisting of linear $C_1$ to $C_{20}$ alkyl, branched $C_3$ to $C_{20}$ alkyl, $C_4$ to $C_{12}$ cycloalkyl, $C_1$ to $C_{20}$ alkyl substituted $C_5$ to $C_{20}$ cycloalkyl, and $C_6$ to $C_{20}$ aryl. More preferably the subtituents (S5) are selected from the group consisting of methyl, ethyl, n-propyl, iso-propyl, n-butyl, tert-butyl, cyclohexyl, and phenyl. Especially preferred subtituents (S5) are linear $C_1$ to $C_{20}$ alkyl or branched $C_3$ to $C_{20}$ alkyl, like —C(CH$_3$)$_3$.

The bridging group of formula (III) or (IV) is preferably the bridging group "—Y(R')(R'')—" of formula (II) as defined above, more preferably
Y is Si and
R' and R'' are independently from each other selected from the group consisting of $C_1$ to $C_{10}$ alkyl, $C_4$ to $C_{10}$ cycloalkyl, and $C_6$-$C_{12}$ aryl.

Said transition metal compounds of formula (I), (III) and (IV) being of metallocene type and their preparation are well known in the art. Metallocenes as defined in the instant invention are particularly preferred.

Alternatively, in a further subgroup of the metallocene compounds, the transition metal (M) bears a "Cp"-ligand as defined above for formula (I), (III) or (IV) and additionally a $\eta^1$- or $\eta^2$-ligand, wherein said ligands may or may not be bridged to each other. This subgroup includes so called "scorpionate compounds" (with constrained geometry) in which the transition metal (M) is complexed by a $\eta^5$-ligand bridged to a $\eta^1$- or $\eta^2$-ligand, preferably $\eta^1$- (for example σ-bonded) ligand, e.g. a metal complex of a "Cp"-ligand as defined above, e.g. a cyclopentadienyl group, which bears, via a bridge member, an acyclic or cyclic group containing at least one heteroatom, e.g. —NR''$_2$ as defined above. Such compounds are described e.g. in WO 96/13529, the contents of which are incorporated herein by reference.

Any alkyl, alkenyl or alkynyl residue referred above alone or as a part of a moiety may be linear or branched, and contain preferably of up to 9, e.g. of up to 6, carbon atoms. Aryl is preferably phenyl or naphthalene. Halogen means F, Cl, Br or I, preferably Cl.

Another subgroup of the transition metal compounds of formula (I) usable in the present invention is known as non-metallocenes wherein the transition metal (M) (preferably a Group 4 to 6 transition metal, suitably Ti, Zr or Hf) has a coordination ligand other than cyclopentadienyl ligand.

The term "non-metallocene" used herein means compounds, which bear no cyclopentadienyl ligands or fused derivatives thereof, but one or more non-cyclopentadienyl $\eta$-, or σ-, mono-, bi- or multidentate ligand. Such ligands can be chosen e.g. from (a) acyclic, $\eta^1$- to $\eta^4$- or $\eta^6$-ligands composed of atoms from Groups 13 to 16 of the periodic table (IUPAC), e.g. an acyclic pentadienyl ligand wherein the chain consists of carbon atoms and optionally one or more heteroatoms from groups 13 to 16 (IUPAC), and in which the open chain ligand may be fused with one or two, preferably two, aromatic or non-aromatic rings and/or bear further substituents (see e.g. WO 01/70395, WO 97/10248 and WO 99/41290), or (b) cyclic σ-, $\eta^1$- to $\eta^4$- or $\eta^6$-, mono-, bi- or multidentate ligands composed of unsubstituted or substituted mono-, bi- or multicyclic ring systems, e.g. aromatic or non-aromatic or partially saturated ring systems, containing carbon ring atoms and optionally one or more heteroatoms selected from groups 15 and 16 of the periodic table (IUPAC) (see e.g. WO 99/10353).

Bi- or multidentate ring systems include also bridged ring systems wherein each ring is linked via a bridging group, e.g. via an atom from groups 15 or 16 of the periodic table (IUPAC), e.g. N, O or S, to the transition metal (M) (see e.g. WO 02/060963). As examples of such compounds, i.a. transition metal complexes with nitrogen-based, cyclic or acyclic aliphatic or aromatic ligands, e.g. such as those described in WO 99/10353 or in the Review of V. C. Gibson at al. "Advances in Non-Metallocene Olefin Polymerization Catalysis" Chem. Rev. 2003, 103, 283315, or with oxygen-based ligands, such as group 4 metal complexes bearing bidentate cyclic or acyclic aliphatic or aromatic alkoxide ligands, e.g. optionally substituted, bridged bisphenolic ligands (see i.a. the above review of Gibson et al). Further specific examples of non-$\eta^5$-ligands are amides, amide-diphosphane, amidinato, aminopyridinate, benzamidinate, azacycloalkenyl, such as triazabicycloalkenyl, allyl, beta-diketimate and aryloxide. The disclosures of the above documents are incorporated herein by reference.

The preparation of metallocenes and non-metallocenes, and the organic ligands thereof, usable in the invention is well documented in the prior art, and reference is made e.g. to the above cited documents. Some of said compounds are also commercially available. Thus, said transition metal compounds can be prepared according to or analogously to the methods described in the literature, e.g. by first preparing the organic ligand moiety and then metallating said organic ligand ($\eta$-ligand) with a transition metal. Alternatively, a metal ion of an existing metallocene can be exchanged for another metal ion through transmetallation.

The molar ratio of aluminium, provided by the aluminoxane (A), and the transition metal (M) is in the range of 1:1 to 10 000:1, preferably from 5:1 to 8 000:1, more preferably from 10:1 to 7 000:1, e.g. 100:1 to 4 000:1.

Typically in case of solid (heterogeneous) catalysts the ratio is from 10:1 to 1000:1, such as 100:1 to 500:1.

The quantity of aluminoxane (A) to be employed in the catalyst system of the invention is thus variable and depends on the conditions and the particular transition metal compound chosen in a manner well known to a person skilled in the art.

The hydrocarbon compound (HC) is preferably liquid. Accordingly it is appreciated that the hydrocarbon compound (HC) is an aromatic hydrocarbon solvent, such as for example toluene, benzene, xylenes, ethylbenzene, cumene, mesitylene or cymene. More preferably the hydrocarbon compound (HC) is toluene.

In one embodiment (variant A) the liquid clathrate (LC) is obtainable by, preferably obtained by,
(i) preparing a solution (SO1) of the (liquid) hydrocarbon compound (HC), the aluminoxane (A) and the organometallic compound (O),
(ii) adding to said solution (SO1) the compound (B),
(iii) obtaining a two phase system (TPS1), the upper phase being a (liquid) hydrocarbon compound (HC) rich phase and the lower phase being the liquid clathrate (LC) phase,
(iv) separating the lower phase being the liquid clathrate (LC) phase from upper phase being the (liquid) hydrocarbon compound (HC) rich phase.

In another embodiment (variant B) the liquid clathrate (LC) is obtainable by, preferably obtained by,
(i) preparing a mixture (M2) of the (liquid) hydrocarbon compound (HC), the aluminoxane (A) and the compound (B),
(ii) adding to said mixture (M2) the organometallic compound (O),
(iii) obtaining a two phase system (TPS2), the upper phase being a (liquid) hydrocarbon compound (HC) rich phase and the lower phase being the liquid clathrate (LC) phase,
(iv) separating the lower phase being the liquid clathrate (LC) phase from upper phase being a (liquid) hydrocarbon compound (HC) rich phase.

According to variant A the aluminoxane (A) is first reacted with the organometallic compound (O) in the (liquid) hydrocarbon compound (HC), as disclosed above, leading to the solution (SO1). The formed solution (SO1) is further reacted with the compound (B) leading to the formation of a two phase system (TPS1) comprising two stable immiscible organic layers, which remain intact such that the upper layer (being the hydrocarbon compound (HC) rich layer) can be separated from the lower liquid clathrate (LC) layer, i.e. the liquid clathrate (LC).

The reaction is performed preferably under stirring and under inert atmosphere of for example $N_2$ or Argon at temperatures between 10 and 40° C., preferably between 15 and 35° C. and more preferably between 20 and 30° C., for example at room temperature.

The upper phase is discarded and the lower liquid clathrate (LC) phase, i.e. the liquid clathrate (LC), is optionally washed before further use. Preferably the liquid clathrate (LC) phase, i.e. the liquid clathrate (LC), is washed once or up to 5 times, preferably once to three times, with the (liquid) hydrocarbon compound (HC), like toluene, used for its preparation.

According to variant B (applies also for variant A) the starting concentration of aluminoxane (A) in the hydrocarbon compound (HC), like toluene, is not particularly critical and usually ranges from 5 to 30 wt.-% solution. For instance methylaluminoxane (MAO) is commercially available as a solution of MAO in toluene.

To this solution the compound (B) is added obtaining the mixture (M2).

Although the use of ambient temperatures is most convenient, i.e. from 0 to 30° C., some compounds require elevated temperatures up to 80° C. or higher. A person skilled in the art can easily determine experimentally a suitable temperature for any of the compounds (B) as defined in detail below.

The mixture (M2) is then reacted, preferably under stirring, with the organometallic compound (O), as described above, under inert atmosphere of for example $N_2$ or Argon at temperatures between 10 and 40° C., preferably between 15 and 35° C. and more preferably between 20 and 30° C., for example at room temperature.

Phase separation into the two phase system (TPS2) may occur immediately, i.e. by mixing the compound (B) with the aluminoxane (A) in the hydrocarbon compound (HC), like toluene, or may commence after a couple of days, i.e. after two or three days. Separation can be improved if the mixture (M2) with the organometallic compound (O) is cooled down to −20° C.

Accordingly the reaction is characterized by the formation of a two phase system (TPS2) comprising two stable immiscible organic layers, which remain intact such that the upper layer (being the hydrocarbon compound (HC) rich layer) can be separated from the lower liquid clathrate (LC) layer, i.e. the liquid clathrate (LC).

Advantageously the aluminoxane (A), like MAO, exclusively resides in the lower phase, i.e. the liquid clathrate (LC), and alkylaluminium, like trimethylaluminium (unreacted starting material from the preparation of aluminoxane (A), like MAO) is extracted into the hydrocarbon compound (HC) rich upper phase, so that the liquid clathrate phase (LC), i.e. the liquid clathrate (LC), like in variant A, contains decreased amount of unreacted trimethylaluminium. The amout of alkylalyminium will depend on clathrate used, it's content in synthesis and the reaction temperature used. A person skilled in art can optimize the synthesis conditions to achieve an optimesed removal of unreacted trimethylaluminium.

For further processing the liquid clathrate (LC) phase, i.e. the liquid clathrate (LC), is separated from the upper solvent layer by conventional separation techniques, for example by decantation or draining.

Optionally the separated liquid clathrate (LC) phase can be washed before further use. Preferably the liquid clathrate phase (LC) is washed once or up to 5 times, preferably once to three times, with the hydrocarbon compound (HC) used for its preparation.

Accordingly the liquid clathrate (LC) as such is used in the precipitation step (B) and not for instance together with the upper phase formed during the preparation of the liquid clathrate (LC).

A further finding of the present invention is that solid catalyst system (CS) particles are obtainable in a convenient and sustainable manner. The liquid clathrate (LC) enables a person skilled in the art either to accomplish precipitation without any solvents or to use during the precipitation the solvents, which are in healthy and safety point of view convenient to be used. Such solvents include e.g. silicon fluids (SF).

It is known from the literature the guest (G) of the liquid clathrate (LC) is important to give the overall liquid clathrate (LC) structure the properties needed. In case the guest (G) is absent, at least partly, the lattice (L) will immediately crystallize. This phenomena is used in the present process to obtain the solid catalyst system (CS) particles.

Accordingly in the instant process precipitation in step (B) is accomplished by removing the hydrocarbon compound (HC) from the liquid clathrate (LC). The removal can be effected by different techniques.

In one aspect of the present invention the liquid clathrate (LC) is precipitated by stripping the hydrocarbon compound (HC) from the liquid clathrate (LC). The stripping of the hydrocarbon compound (HC) can be accomplished by dropping pressure and/or changing temperature.

Pressure and/or temperature changes in said stripping method are highly dependent on each other, as well the solvents used. The pressure and/or temperature needed can be adjusted by the person skilled in the art without any inventive effort. After precipitation the obtained particles can be grinded if desired.

In another embodiment the precipitation in step (B) is accomplished by introducing the liquid clathrate (LC) into a solvent (S) which causes a dilution effect for the guest (G), i.e. the hydrocarbon compound (HC). This dilution effectuates that the hydrocarbon compound (HC) is removed from the liquid clathrate (LC), which in turn leads to the precipitation of the catalyst system (CS).

In principle any solvents (S) can be used to accomplish the precipitation of the liquid clathrate (LC), including halogenated and non-halogenated hydrocarbons, as long as the hydrocarbon compound (HC) is soluble in the solvent (S) and thus a dilution effect is achieved.

However a specific finding of the present invention is that non-halogenated solvents can be employed and are useful in the present method, which are in preparation point of view much more convenient solvents than many halogenated solvents are. Normally such solvents cannot be employed in the precipitation processes of catalyst systems according to this invention as the catalyst systems are normally soluble therein.

Accordingly a further important aspect of the present invention is the specific selection of solvent (S) which enables precipitation of the catalyst system (CS) from the liquid clathrate (LC) with less harmful solvents. Such suitable solvent (S) comprises, preferably is, a silicon fluid (SF). If a mixture is used as solvent (S), the amount of silicon fluid (SF) within the solvent (S) is at least 50 vol.-%, yet more preferably at least 70 vol.-%, at least 80 vol.-%, like at least 90 vol.-%.

Thus in a preferred embodiment the precipitation in step (B) is accomplished by introducing the liquid clathrate (LC) into a solvent (S) comprising a silicon fluid (SF), preferably into a solvent (S) being a silicon fluid (SF).

Further the solvent (S), preferably the silicon fluid (SF), is also inert in relation to the compounds of the solid catalyst system to be produced. The term "inert in relation to the compounds" means herein that the solvent (S), preferably the silicon fluid (SF), is chemically inert, i.e. undergoes no chemical reaction with any solid catalyst system forming compound or catalyst system precursor forming compound (e.g. the organometallic compound (O) and the aluminoxane (A)).

The solvent (S) as whole as well as the silicon fluid (SF) as such differs from the organo-silicon compound (OS), which is preferably used as the compound (B) when generating the liquid clathrate (LC).

A silicon fluid (SF) according to this invention is understood as known in the art. Reference is made inter alia to Ullmann's Encyclopedia of Industrial Chemistry 1993, Vol. A24, pages 57 to 93. Accordingly a silicon fluid (SF) according to this invention has preferably (a) a weight average molecular weight (Mw) of 300 to 50,000 g/mol, more preferably of 1,000 to 30,000 g/mol, like 5,000 to 15,000 g/mol, and/or (b) a viscosity at 25° C. of at least 10 cSt, more preferably in the range of 10 to 1500 cSt.

Preferred silicon fluids (SF) are those selected from the group consisting of methylsilicon fluid, methylphenylsilicon fluid, methylhydrogensilicon fluid, and mixtures thereof. More preferably the silicon fluid (SF) comprises, yet more preferably consists of, a methylsilicon fluid.

In one specific preferred embodiment the silicon fluid (SF) is a methylsilicon fluid having (a) a weight average molecular weight (Mw) of 300 to 50,000 g/mol, more preferably of 1,000 to 30,000 g/mol, like 5,000 to 15,000 g/mol, and/or (b) a viscosity at 25° C. in the range of 10 to 1200 cSt, more preferably in the range of 50 to 800 cSt, like 100 to 300 cSt.

Such silicon fluids (SF) are commercially available, for instance from Dow Corning and sold under the trade name Dow Corning 200® Fluids. However, the invention is not restricted to these commercial products, but any silicon fluids (SF) fulfilling the requirements of the present invention can be used as well.

The transfer of the liquid clathrate (LC) into the solvent (S), preferably into the silicon fluid (SF), can be accomplished known in the art, for instance by pouring the liquid clathrate (LC) into the solvent (S), preferably into the silicon fluid (SF). Typically after transfer the obtained mixture is agitated (stirred) to facilitate the formation of the solid catalyst system (CS) particles. No specific temperature is needed. Solidification can be accomplished in a broad temperature range, like 2 to 80° C. Optimal temperature is dependent on the viscosity of used fluid, like silicon fluid (SF). By selecting fluids with different viscosities the optimal precipitating temperature can vary e.g. from below 0 to above 100° C., i.e. the operating window can be broadened. Very good results are achievable at temperatures between 18 to 28° C., like 20 to 24° C., if fluids having viscosity in the range of 100 to 200 cSt are used.

Due to the dilution of the hydrocarbon compound (HC) the solidification of the liquid clathrate (LC) is effected and yields to the formation of the solid catalyst system (CS), which in turn leads to a suspension.

Alternatively the liquid clathrate (LC) is introduced very fast into the solvent (S), preferably into the silicon fluid (SF), typically by spray-technology. This way of forming the catalyst system (CS) particles has the advantage that very spherical particles are obtained compared to simple pouring technique.

The solid catalyst system (CS) particles which are obtained by the precipitation step (B) may be separated and recovered by any procedure known in the art from the suspension. For example, the suspension may be filtered. Other commonly known methods for isolating are decanting, centrifuging and flotation. The catalyst system (CS) may then be optionally washed and/or dried to remove any solvent residuals present in the particles. The washing and/or drying of the catalyst particles may be carried out in any manner conventional in the art.

The instant process leads to a solid catalyst system (CS), in particular to solid catalyst system (CS) without any need of using external support material.

Further the present invention is directed to the use of the solid catalyst system (CS) as defined herein for the preparation of a polymer, like polypropylene or polyethylene.

The present invention is further described by way of examples.

EXAMPLES

1. Definitions/Measuring Methods

The following definitions of terms and determination methods apply for the above general description of the invention as well as to the below examples unless otherwise defined.

Viscosity has been measured according to ASTM D445-09, and denotes kinematic viscosity ICP Analysis The elemental analysis of a catalyst was performed by taking a solid sample of mass, M, cooling over dry ice. Samples were diluted up to a known volume, V, by dissolving in nitric acid ($HNO_3$, 65%, 5% of V) and freshly deionised (DI) water (5% of V). The solution was then added to hydrofluoric acid (HF, 40%, 3% of V), diluted with DI water up to the final volume, V, and left to stabilize for two hours.

The analysis was run at room temperature using a Thermo Elemental IRIS Advantage XUV Inductively Coupled Plasma-Atomic Excitation Spectrometer (ICP-AES) which was calibrated immediately before analysis using a blank (a solution of 5% $HNO_3$, 3% HF in DI water), a low standard (10 ppm Al in a solution of 5% $HNO_3$, 3% HF in DI water), a high standard (50 ppm Al, 50 ppm Hf, 20 ppm Zr in a solution of 5% $HNO_3$, 3% HF in DI water) and a quality control sample (20 ppm Al, 20 ppm Hf, 10 ppm Zr in a solution of 5% $HNO_3$, 3% HF in DI water).

The content of transition metal was monitored using the 282.022 nm and 339.980 nm lines and the content for zirconium using 339.198 nm line. The content of aluminium was monitored via the 167.081 nm line, when Al concentration in ICP sample was between 0-10 ppm and via the 396.152 nm line for Al concentrations between 10-100 ppm. The reported values, required to be between 0 and 100, or further dilution is required, are an average of three successive aliquots taken from the same sample and are related back to the original catalyst using equation 1.

$$C = \frac{R \times V}{M} \quad \text{Equation 1}$$

wherein
C is the concentration in ppm, related to % content by a factor of 10,000
R is the reported value from the ICP-AES
V is the total volume of dilution in ml
M is the original mass of sample in g
If dilution was required then this also needs to be taken into account by multiplication of C by the dilution factor.

Chemicals Used:
MAO
was purchased from Albemarle and used as a 30 wt-% solution in toluene.
Metallocene 1
rac-ethylene-bis[(2-tert-butyldimethylsiloxy)indenyl]zirconium dichloride, Preparation according to U.S. Pat. No. 6,277,778 B1
Metallocene 2
rac-dimethylsilanediyl-bis[(2-methyl-4-phenyl)-indenyl]$_2$ zirconium dichloride, Producer NORQUAYTECH, CAS No: 153882-67-8
Silicon Fluid:
DOW CORNING 200® Fluid, viscosity 100 cSt
OMTS:
Octamethyltrisiloxane Mw 236.53 g/mol, CAS 107-51-7, ALDRICH product No: 235709

2. Preparation of the Examples

2. Preparation of Catalyst System

Example 1

Preparation of Metallocene/MAO Complex Solution 216.3 mg of metallocene 1 and 15 ml MAO (30% solution in toluene) containing 13.28 w % aluminium, were mixed 60 min (a bright yellow solution was formed).

Preparation of Liquid Clathrate

Into previously prepared complex solution 1.0 ml of octamethyltrisiloxane (OMTS) was added and the reaction mixture was stirred over weekend at room temperature (20 to 25° C.). After 96 h stirring was stopped and separation of the complex solution into two phases was clearly seen. The upper phase (toluene) was removed and the lover clathrate phase was washed once with 5 ml toluene.

Precipitation of Clathrate

Figure 1:
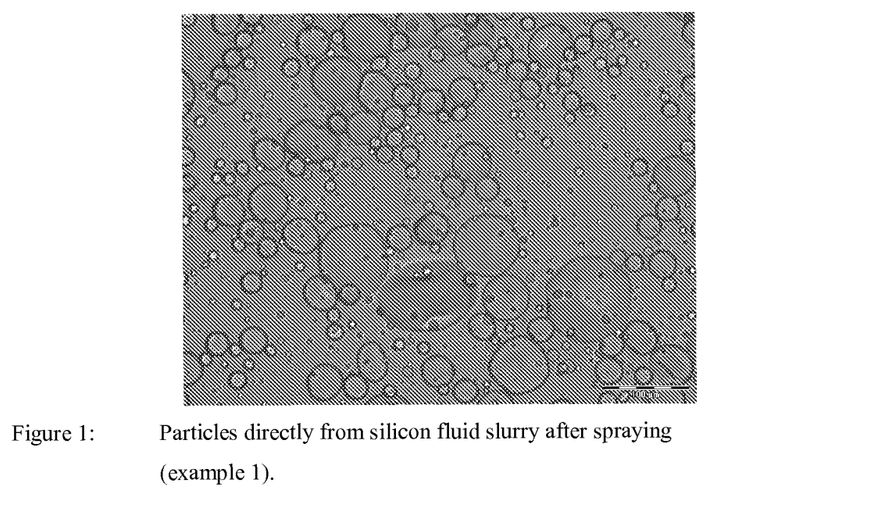
FIG. 1: Particles directly from silicon fluid slurry after spraying (Example 1).
Figure 2:
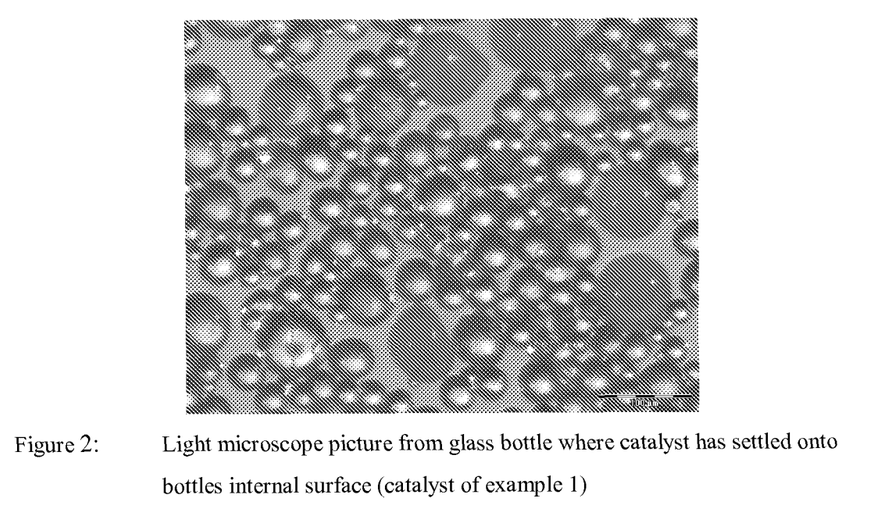
FIG. 2: Light microscope picture from glass bottle where catalyst has settled onto bottles internal surface (catalyst of Example 1).
Figure 3:
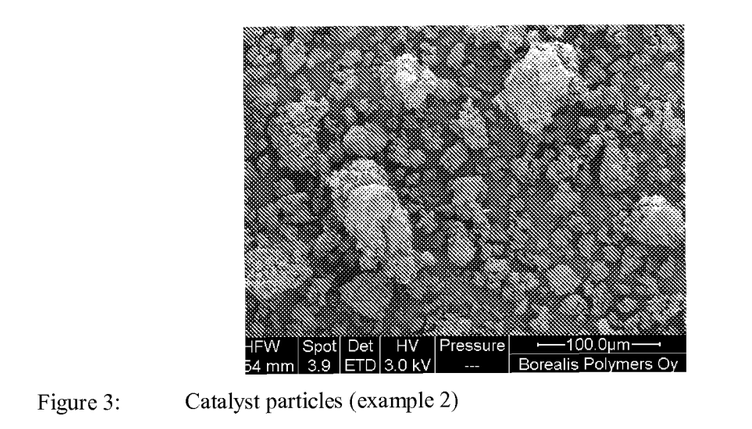
FIG. 3: Catalyst particles (Example 2).
Figure 4:
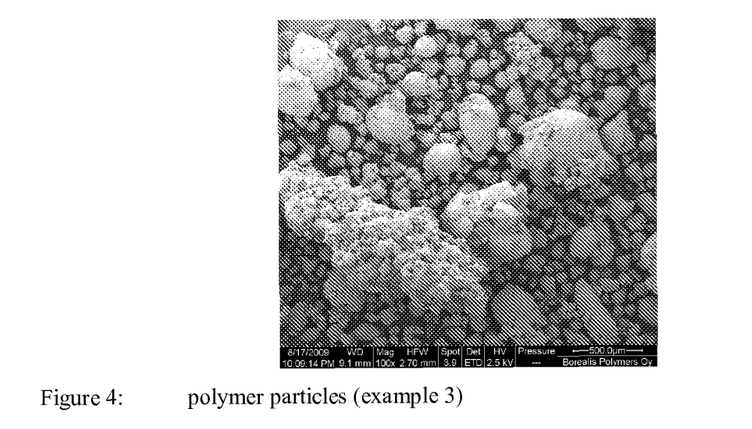
FIG. 4: Polymer particles (Example 3).

The obtained liquid clatherate was added slowly, (drop by drop) into the silicon fluid having the viscosity of 100 cSt (not containing any toluene). Particles with rather large particle size but still very nice spherical appearance formed immediately indicating clearly that liquid clathrate was precipitating very easily. When addition speed was increased (fast injection by using small needle and vigorous stirring of receiving vessel (traditional septa bottle) surprisingly nice particle morphology is achieved. The particles are solid, spherical, and even particle sizes are surprisingly similar (see FIG. 1)

Example 2

Preparation of Metallocene/MAO Complex Solution

Septa bottle containing 130 mg of metallocene 2 and 10 ml MAO (30% solution in toluene), with Al 13.28 wt.-%, were mixed 60 min (a bright red solution formed).

Preparation of Liquid Clahtrate

Into the previously prepared complex solution 0.97 ml of octamethyltrisiloxane (OMTS) was added and the reaction mixture stirred overnight at room temperature. After 24 h stirring was stopped and separation of complex solution into two phases takes place.

Precipitation of Clathrate

The upper phase (mainly toluene) was removed, and the lover clathrate phase was transferred into the 50 ml glass flask. The mixture was dried in vacuum at 50° C. together with argon flow for 4 hours for removal of the toluene residues. Solid particles were obtained.

Example 3

Polymerization

A 5 liter stainless steel reactor was used for propylene polymerizations. 1100 g of liquid propylene (Borealis polymerization grade) was fed to the reactor. 0.2 ml triethylaluminum (100%, purchased from Crompton) was fed as a scavenger and 15 mmol hydrogen as chain transfer agent. Reactor temperature was set to 30° C. 23.1 mg of catalyst of example 2 was flushed into to the reactor with nitrogen overpressure and 5 ml PFC. The reactor was heated to 70° C. in a period of about 15 minutes. After 30 min polymerisation time the propylene was flushed out and the polymer was dried and weighted. The polymer yield was 29 g. Catalyst activity was 2.5 kgPP/g cat h.

We claim:

1. A process for the preparation of a solid catalyst system (CS) comprising the steps of
(I) preparing a liquid clathrate (LC) comprising
  (i) a lattice (L) being the reaction product of
    (α) aluminoxane (A),
    (β) an organometallic compound (O) of a transition metal (M) of Group 3 to 10 of the Periodic Table (IUPAC 2007) or of an actinide or lanthanide, and
    (γ) a compound (B) being effective to form with the aluminoxane (A) and the organometallic compound (O) the lattice (L),
  and
  (ii) a guest (G) being an hydrocarbon compound (HC), and subsequently followed by
(II) precipitating said liquid clathrate (LC) to obtain said solid catalyst system (SC),
wherein said process does not comprise a step in which the liquid clathrate (LC) is emulsified.

2. The process according to claim 1, wherein the liquid clathrate (LC) is obtained by
  (i) preparing a solution (SO1) of the hydrocarbon compound (HC), the aluminoxane (A) and the organometallic compound (O),
  (ii) adding to said solution (SO1) the compound (B),
  (iii) obtaining a two phase system (TPS1), the upper phase being a hydrocarbon compound (HC) rich phase and the lower phase being the liquid clathrate (LC) phase,
  (iv) separating the lower phase being the liquid clathrate (LC) phase from upper phase being the hydrocarbon compound (HC) rich phase.

3. The process according to claim 1, wherein the liquid clathrate (LC) is obtained by
  (i) preparing a mixture (M2) of the hydrocarbon compound (HC), the aluminoxane (A) and the compound (B),
  (ii) adding to said mixture (M2) the organometallic compound (O),
  (iii) obtaining a two phase system (TPS2), the upper phase being a hydrocarbon compound (HC) rich phase and the lower phase being the liquid clathrate (LC) phase,
  (iv) separating the lower phase being the liquid clathrate (LC) phase from upper phase being a hydrocarbon compound (HC) rich phase.

4. The process according to claim 1, wherein the precipitation of step (II) is accomplished by removing the hydrocarbon compound (HC) from the liquid clathrate (LC).

5. The process according to claim 1, wherein the precipitation of step (II) is accomplished by introducing the liquid clathrate (LC) into a silicon fluid (SF).

6. The process according to claim 5, wherein the introduction is accomplished by spraying the liquid clathrate (LC) into the silicon fluid (SF).

7. The process according to claim 1, wherein the hydrocarbon compound (HC) is an aromatic hydrocarbon.

8. The process according to claim 5, wherein the silicon fluid (SF) is selected from the group consisting of methylsilicon fluid, methylphenylsilicon fluid, methylhydrogensilicon fluid, and mixtures thereof.

9. The process according to claim 1, wherein the compound (B) is an M-X compound or an organo-silicon compound (OS) being different to the silicon fluid (SF).

10. The process according to claim 9, wherein the M-X compound is an organic, inorganic or organometallic compound which can dissociate into cationic and anionic components and
"M" is an alkali earth metal or alkaline earth metal, and
"X" is selected from the group consisting of halide, pseudohalide, allylic hydrocarbon group, and benzylic hydrocarbon group.

11. The process according to claim 9, wherein the M-X compound is selected from the group consisting of KCl, KF, NaF, KH, LiH, KOSiMe$_3$, NaBPh$_4$, Me$_4$NCl, (Octyl)$_3$NClMe, MePh$_3$PBr, KB(C$_6$F$_5$)$_4$, and KCH$_2$—C$_6$H$_5$.

12. The process according to claim 9, wherein the organosilicon compound (OS) is selected from the group consisting of hydrocarbyloxysilanes of the formula $R_3Si\text{—}O[\text{—}SiR_2\text{—}O]_n\text{—}SiR_3$ or $Si\text{—}[O\text{—}R]_4$ wherein R is, independently, a hydrocarbyl group having up to about 18 carbon atoms and n is 0 to 3; and hydrocarbylpolysiloxanes having from 2 to 6 silicon atoms in the molecule and which are separated from each other by an oxygen atom such that there is a linear, branched or cyclic backbone of alternating Si and oxygen atoms, with the remainder of the four valence bonds of each of the silicon atoms individually satisfied by an univalent hydrocarbyl group, R as defined for the hydrocarbyloxysilanes.

13. The process according to claim 1, wherein the organometallic compound (O) of the transition metal (M) is a compound of formula (I)

$$(L)_m R_n MX_q \quad (I)$$

wherein

"M" is a transition metal as defined in claim 1 each "X" is independently a σ-ligand, each "L" is independently an organic ligand which coordinates to the transition metal (M), "R" is a bridging group linking said organic ligands (L), "m" is 2 or 3, "n" is 0, 1 or 2, "q" is 1, 2 or 3, m+q is equal to the valency of the transition metal (M).

14. The process according to claim 1, wherein the hydrocarbon compound (HC) is toluene.

15. The process according to claim 13, wherein "m" is 2.

16. The process according to claim 13, wherein "n" is 1.

* * * * *